United States Patent
van Dijk (10) Patent No.: US 6,399,844 B1
(45) Date of Patent: Jun. 4, 2002

(54) FIXED BED PROCESS FOR CONVERSION OF METHANOL WITH SILICO ALUMINA PHOSPHATE MOLECULAR SIEVE CATALYST

(75) Inventor: Christian P. van Dijk, Houston, TX (US)

(73) Assignee: Van Dijk Technologies, Inc., Houston, TX (US)

( * ) Notice: Subject to any disclaimer, the term of this patent is extended or adjusted under 35 U.S.C. 154(b) by 0 days.

(21) Appl. No.: 09/509,252

(22) PCT Filed: Sep. 21, 1998

(86) PCT No.: PCT/US98/19535

§ 371 (c)(1),
(2), (4) Date: Jul. 25, 2000

(87) PCT Pub. No.: WO99/15482

PCT Pub. Date: Apr. 1, 1999

Related U.S. Application Data (60) Provisional application No. 60/060,702, filed on Sep. 24, 1997.

(51) Int. Cl.[7] ................................................. C07C 1/20
(52) U.S. Cl. ......................... 585/639; 585/638; 585/640
(58) Field of Search ................................. 585/638, 639, 585/640

(56) References Cited

U.S. PATENT DOCUMENTS

| | | |
|---|---|---|
| 4,404,414 A | 9/1983 | Penick et al. ............... 585/469 |
| 4,654,453 A | 3/1987 | Tabak ......................... 585/303 |
| 5,602,289 A | 2/1997 | Van Dijk .................... 585/315 |

Primary Examiner—Walter D. Griffin
(74) Attorney, Agent, or Firm—Akin, Gump, Strauss, Hauer & Feld, L.L.P.

(57) ABSTRACT

A process for converting methoxy compounds, like methanol or dimethyl ether, into olefins, preferably ethylene, by contacting such methoxy compounds over a series of fixed catalyst beds.

4 Claims, 2 Drawing Sheets

FIXED BED PROCESS FOR CONVERSION OF METHANOL WITH SILICO ALUMINA PHOSPHATE MOLECULAR SIEVE CATALYST

CROSS-REFERENCE TO RELATED APPLICATIONS

This applications claims benefit of and priority to U.S. Provisional Application Ser. No. 60/060,702, filed Sep. 24, 1997, for which the inventor and title are the same as the present patent application.

STATEMENTS REGARDING FEDERALLY SPONSORED RESEARCH OR DEVELOPMENT

Not applicable.

REFERENCE TO A MICROFICHE APPENDIX

Not applicable.

BACKGROUND OF THE INVENTION

1. Field of the Invention

This invention relates to a process for converting methoxy compounds, like methanol or dimethyl ether, into olefins, preferably ethylene, by contacting such methoxy compounds over a series of fixed catalyst beds.

2. Description of the Related Art

A new family of molecular sieve catalysts has been developed by Union Carbide workers. See U.S. Pat. No. 4,499,327. These silico alumino phosphate molecular sieve catalysts have demonstrated a high activity for converting methoxy compounds like methanol and/or dimethyl ether into olefin mixtures. Unlike earlier ZSM-5 catalysts which convert methoxy compounds to liquid grade hydrocarbons of a gasoline range (methanol to gasoline; or MTG), these new molecular sieve catalysts for conversion of methanol to olefins are more selective to the conversion of methanol to $C_{2-4}$ olefins (MTO) and produce a lower concentration of higher carbon number alkylate and aromatic by-products. Based upon the carbon content of the feedstock, these new methanol to olefin (MTO) catalysts produced high yields of $C_{2-4}$ olefinic materials.

Even so, with the new (MTO) catalysts, the formation of aromatics ($C_{6+}$) is not completely suppressed. Because of the molecular size of aromatic by-products, once formed, they can not readily pass through the pore structure of the Zeolite catalyst. Such aromatics as are formed, which are thus effectively trapped against further free passage through the catalyst pores, are believed to undergo further reactions to ultimately yield coke. Hence, even with the new (MTO) catalyst, if used in a fixed bed operation, such catalyst has a very short active life before regeneration of the catalyst becomes necessary. Time on stream (TOS) of a fixed bed of MTO catalyst was initially measured in hours only. Such a short operational time on stream, obviously, is not acceptable as a basis for a commercial operation; because of the need to regenerate the catalyst after its activity has deteriorated. For safety reasons, when a catalyst reaction vessel is taken out of service for regeneration of the catalyst therein, the process shutdown period must be much longer than the few hours needed to simply regenerate the catalyst.

Many factors have been considered in an attempt to prolong the useful catalyst life of the new MTO catalyst for use in a fixed bed operation. Lowering of the partial pressure of the methoxy compound in contact with the MTO catalyst was examined as one possible means of prolonging the useful active catalyst life. Although lowering the partial pressure of methanol over the MTO catalyst was found to prolong the period of time for which the MTO catalyst was active, it was also discovered that the rate at which methoxy compound converted over the MTO catalyst was also reduced as a function of reducing partial pressure of the methoxy compound in essentially an inverse relationship to the period of time by which the MTO catalyst activity was prolonged. The end result of this inverse relationship is that the total amount of olefin product make during the increased TOS (time on stream) of the catalyst remained essentially unchanged. That is, the total quantity of olefin product made between catalyst regenerations (the TOS period) remains essentially the same whether the time on stream (TOS) was short because of a high initial partial pressure of the methanol feed or long because of a low initial partial pressure of the methanol feed. In other words, the degree to which the methanol feed to a one pass single fixed bed of MTO catalyst was diluted by a non-reactive component, such as steam or a non-reactive hydrocarbon, was found to be an ineffective parameter by which to increase or control the final yield of olefin product during the on steam operational time of the MTO catalyst.

While market conditions may vary at any particular point in time, on average ethylene is a much more valuable product than other higher olefins like propylene or butylene. Hence, it is of a long run concern that the yield of ethylene as based upon carbon feed input is maximizable compared to that input carbon which is diverted into higher olefins like propylene or butylene. With the new MTO catalyst, it has been demonstrated that ethylene is the product olefin first made upon initial contact of methoxy compound with the catalyst, but that on further contact of the ethylene make with the catalyst, the ethylene initially made is converted into other olefins like propylene and/or butylene. In a one pass process, wherein methoxy compound is passed only one time over a fixed catalyst bed at a high conversion rate of the methanol, the by-reactions which deplete the initial ethylene make by conversion of same to other higher olefins become most pronounced at high methanol conversion levels; that is when methanol conversion exceeds about 90%.

Given the so demonstrated short TOS of the new MTO catalyst at high conversion rates that equate to acceptable olefin yield rates, when considered for fixed bed operations, an inclination would be to use a high MTO catalyst inventory—much more than the minimum quantity of MTO catalyst required for an acceptable methanol conversion—so that upon aging of the MTO catalyst mass from the inlet to outlet side of the reaction vessel there will remain a MTO catalyst zone of sufficient activity to continue operation at acceptable conversion rates of the feed MeOH. That is, the mass-volume of the MTO catalyst inventory undergoes a progressive volume zone aging which proceeds from the feed input, wherein methoxy compound partial pressure is at its highest level, and thus coking is at its highest rate, to that point within the catalyst mass volume inventory at which there is essentially no methoxy compound partial pressure because of its essentially complete conversion at this point within the catalyst mass (about 90% of methanol conversion), after which no significant coking occurs in the catalyst mass after this point. This zone of aging catalyst moves progressive through the fixed catalyst bed and as the leading edge of this zone becomes catalytically inactive due to its high coking level, until such time as that zone of catalyst closest to the product outlet side of the reactor has, through the width of its mass of this zone, undergone such aging/coking as to reduce its activity below acceptable levels. At this point in time, a fixed bed reactor of the MTO catalyst would be taken out of operation and its entire inventory of MTO catalysts would have to be regenerated to restore its activity. This, today, is the only expedient for utilizing the new MTO catalyst in a fixed bed operation such that the reactor could possibly operate for an acceptable period of time at practical olefin production rates. However, as one will readily appreciate, there is a high capital cost involved in this expedient for extending TOS. Further, in this single bed-one pass-high conversion-mode of operation there is no capability for controlling the degree of methanol conversion—the degree of conversion will always by high, $\geq 95\%$, and typically about 99%. As previously noted, at such high degrees of methanol conversion significant amounts of the ethylene make is diverted by side reactions into production of propylene and/or butylene.

Further, with fresh, or freshly regenerated catalysts, as would be the case with the regeneration of that mass of MTO catalyst within a one pass single fixed bed, the initial ethylene production of the regenerated MTO catalyst is very low. It was found that as a reasonable amount of coke is deposited on the catalyst, the ethylene yield is actually increased substantially. A. N. Rene Bos et al. Conversion of Methanol to Lower Olefins, *Ind. Engl. Chem. Res.*, 1995 Vol. 34, pp. 3808–3816. The coke formed at high temperature on such MTO catalysts is most likely due to the formation of small amounts of aromatics which, becoming entrapped in the small pores of the catalyst, become further highly methylated at high temperatures. A further coke forming process of consequence to the MTO catalyst is that of polymerization of olefins at lower temperatures.

Given all of the shortcomings of the new MTO catalyst it is not surprising that at an early point in time the Union Carbide researchers, who developed this particular MTO catalyst, discounted the possibility of proceeding practically with a fixed bed operation with this catalyst and, instead, switched their attention to a fluidized bed process with this MTO catalyst. A fluidized bed operation for utilization of this MTO catalyst has also been pursued by UOP and Norsk Hydro.

A fluidized bed operation overcomes a further drawback of this MTO catalyst, that being one of a high pressure drop occasioned by the fine power nature in which the new MTO catalyst is formed.

It is desirable to devise a process which would allow the new MTO catalyst to be utilized in a fixed catalyst bed procedure, especially if its utilization in a fixed bed mode could provide a higher ethylene yield than is presently possible with those fluidized bed operations now proposed.

BRIEF SUMMARY OF THE INVENTION

This invention comprises a process for converting methoxy compounds in the presence of a diluent, preferably steam or steam and/or a non-reactive organic compound, by passing the methoxy feed compound into multiple contacts with fixed beds of MTO catalyst in a series of fixed bed reactors. The feed rates of the methoxy compound is such, that in each of the reactors in series only a partial reaction of the methoxy compound is taking place to at least 80% of the total methoxy amount fed to that reactor. The advantage of only feeding a fraction of the total methoxy compound to a single reactor stage is that in that reactor the potential adiabatic temperature rise is reduced considerably. In the following reactors the methoxy compounds can be fed at lower than reaction temperature, thus reducing the inlet temperature of the total gas mixture into that reactor stage. A further reduction of the adiabatic temperature rise is possible by recycle of the effluent of a reactor stage.

Therefore, in a preferred version of the invention, a quantity of methoxy compound is added as fresh feed to each of the series of back-mixed fixed bed MTO catalyst reactors, wherein a portion of the product gas composition of this reactor is recycled back to the feed inlet of this particular reactor as a portion of its total feed and a remainder portion, or a bleed portion of the product gas composition of this, or any one reactor is passed as feed to the next in series, thus building up ethylene partial pressure through the series of reactors gradually, from stage to stage, while maintaining a low partial pressure of methoxy compound in any one of the series reactor.

In each back-mixed reactor stage the partial pressure of the total methoxy compound, measured as an equivalent to methanol, is kept at between 0.02 and 0.2 atmospheres absolute (ata). For purposes of this partial pressure calculation of methoxy partial pressure, one unit of dimethyl ether is counted as if it were instead two units of methanol. The total pressure in any reactor of the series is also low, between 0.5 and 3 ata. The employment of a low total reactor pressure makes it acceptable to utilize large surface areas for the MTO catalyst in each reactor, which eliminates the danger of too great a pressure drop across any reactor, especially with the large product gas recycle over each reactor stage. A large volume of reactor product gas recycled back through the feed inlet to that reactor stage is necessary in order to achieve a close approach to total back-mixing within that particular fixed bed reactor. In the back-mix with recycle product gas from a reactor to form the total feed to this particular fixed bed reactor, of the total methanol fed into contact with the MTO catalyst therein, only a small percentage of the total methanol undergoes conversion to olefin products, on the order of 6–10%. Yet, on the basis of fresh feed methanol added to such reactor, especially to those reactors after the first reactor, the conversion of methanol is high, on the order of at least 90%. By this sequence wherein, in each reactor of the series of the total methanol passed through such reactor the conversion is low but relative to the fresh methanol added to such reactor the conversion is high and of such the selectivity of converted methanol into ethylene is enhanced; while overall production of ethylene product by the sequence of two or preferably three or four back-mixed fixed bed MTO catalyst reactors is maintained to a comparable or greater level per unit time as that theoretically possible per unit time with a one pass-single fixed bed MTO catalyst bed. This while with the two, three and/or four fixed bed back-mixed sequence the TOS of the MTO catalyst inventory as a sum of this series of fixed bed reactors, is greatly enhanced such that the quantity of ethylene produced as a function of the MTO catalyst inventory TOS is thus greatly enhanced.

DETAILED DESCRIPTION OF THE INVENTION

Figure 1:
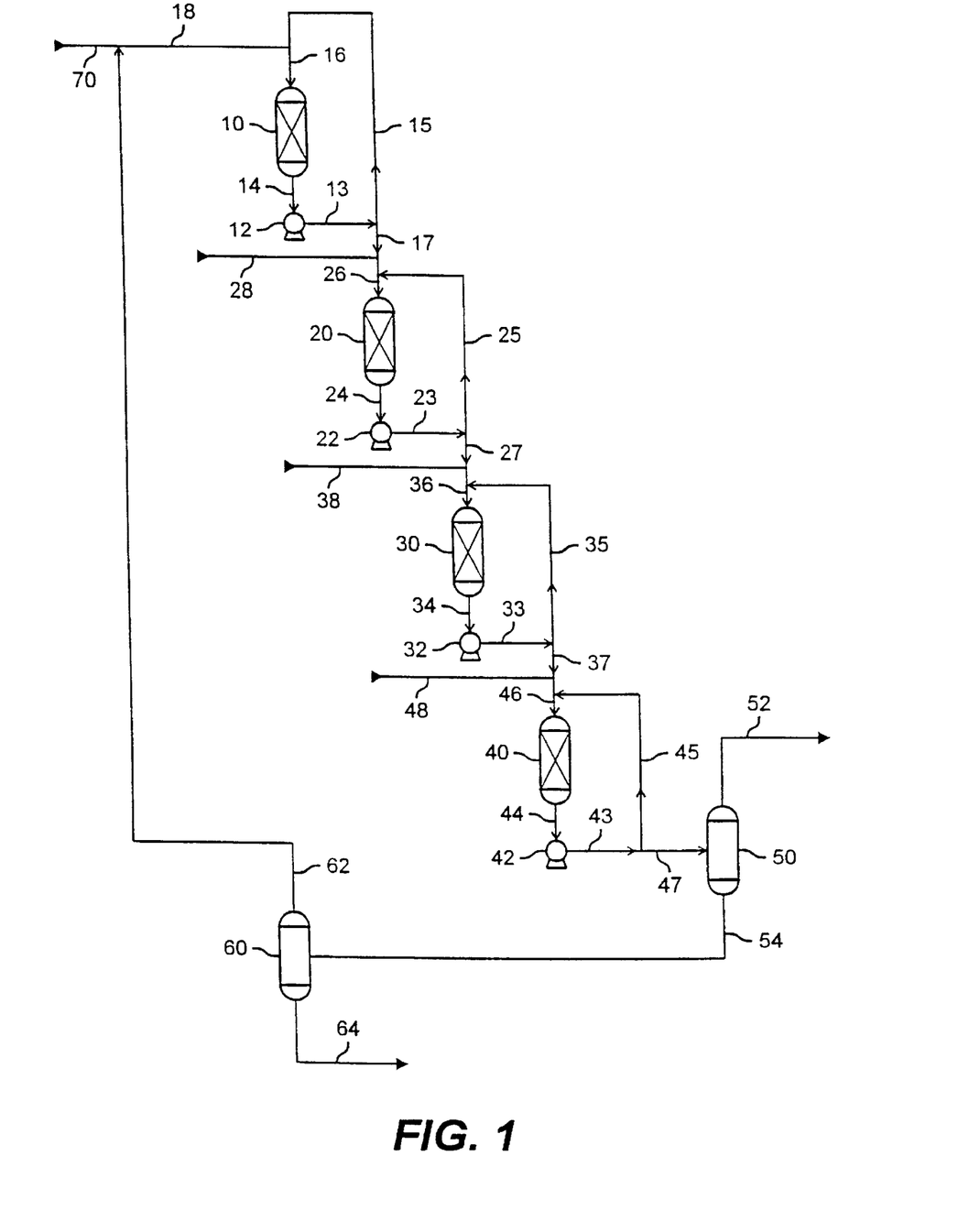
FIG. 1 schematically illustrates a series of four back-mixed fixed MTO catalyst bed reactors following the last of which a portion of the product gas is routed to an olefin stripper with the aqueous methanol bottoms therefrom routed to a methanol stripper to produce a methanol overhead stream having that content of steam desired as a diluent to condition it a fresh feed for cycle back to the inlet of the first reactor. In this sequence the hot recycle fans are positioned to compensate for the pressure drop from the inlet of the first reactor to the outlet of the last reactor such that the total pressure drop across the whole of the series is like that of any one reactor of the series.
Figure 2:
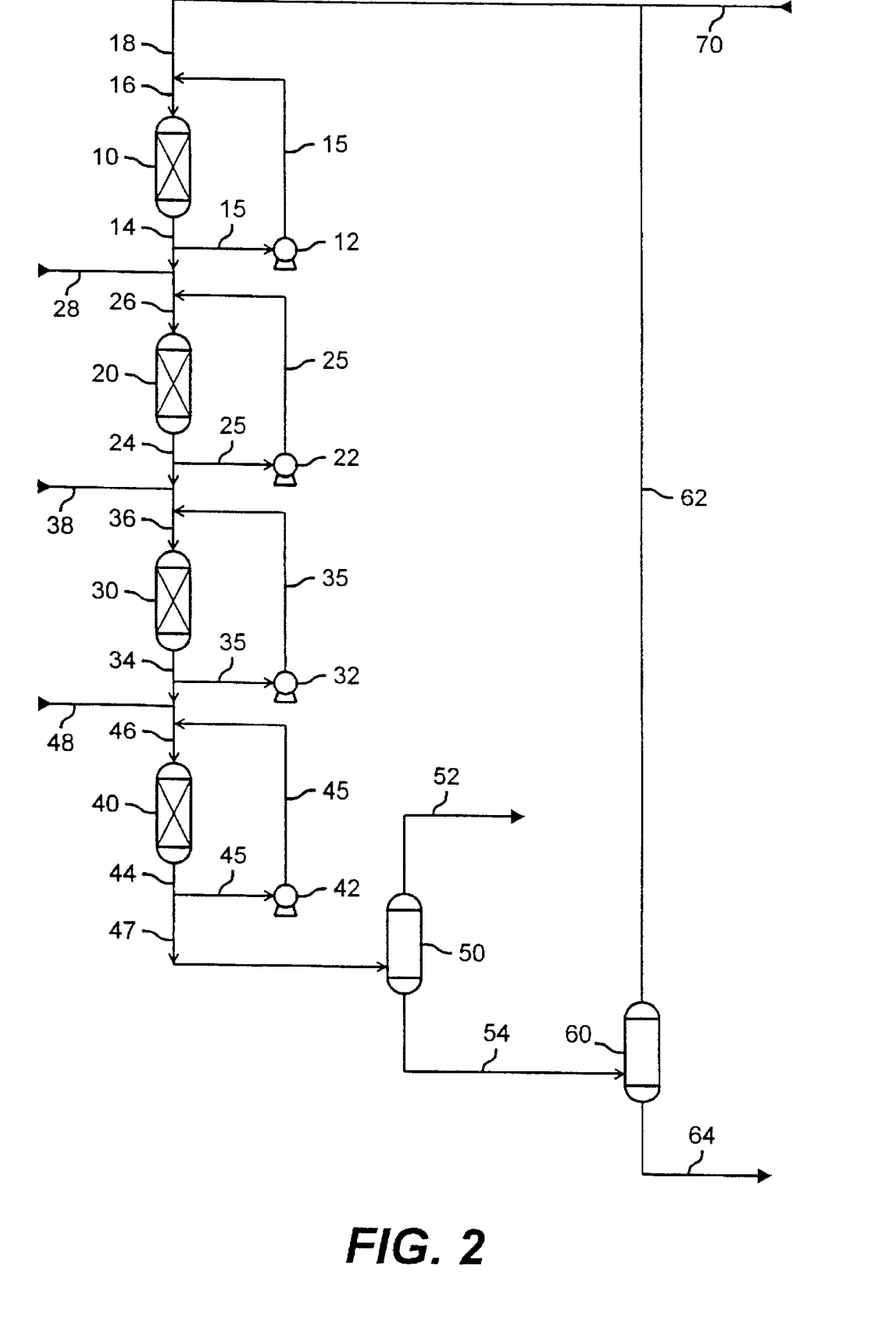
FIG. 2, like FIG. 1, also schematically illustrates a series of four back-mixed fixed MTO catalyst bed reactors with an olefin and methanol stripper following the last reactor. In this sequence there occurs a slight pressure drop across each reactor which sums to the total pressure drop across the series.

FIGS. 1 and 2 illustrate a series of four back-mixed reactors 10, 20, 30 and 40 whereby a hot fan associated to each 12, 22, 32 and 42 respectively, recycles a substantial portion of the exit product gas composition therefrom, 14, 24, 34 and 44 respectively, back to the inlet side of their reactor, 16, 26, 36 and 46 respectively. To the first reactor 10, a quantity of methoxy compound mixed with a diluent, preferably steam, is supplied by line 18 to become admixed with the recycled product gas composition supplied by line 15 and this mixture is fed into the first reactor 10 by line 16. In FIG. 1 product gas formed in reactor 10 exits the reactor by line 14 and is in its entirety slightly recompressed by hot fan 12 and passed there from by line 13 to a split point at which a portion is returned by line 15 to the inlet of reactor 10 and a bleed portion of this product gas is passed by line 17 to the inlet 26 of the second reactor 20. In like manner to first reactor 10, a portion of the product gas composition formed in reactor 20 is recycled by hot fan 22 and line 25 back to the inlet 26 and becomes admixed with a fresh quantity of methanol supplied by line 28 and the bleed product 17 from first reactor 10 to form the total feed for reactor 20 which is fed by inlet line 26. Third reactor 30 operates in a manner analogous to that of reactor 20 respecting hot fan 32 and recycle of a portion of product gas 34 by line 35 back to inlet 36 wherein it becomes admixed with bleed product 27 from reactor 20 and a quantity of fresh methanol 38 to form the total feed to reactor 30. Reactor 40 operates in a manner analogous to that of either of reactors 20 or 30, except bleed product 47 thereof is passed as feed to an olefin stripper 50 to produce as an overhead stream 52 the olefin compositions and as a bottom stream 54 an aqueous methanol composition. The olefin composition 52 is treated in a conventional manner to recover its ethylene, propylene and butylene contents as separate products. The aqueous methanol stream is passed by line 54 to a methanol stripper 60 to produce as an overhead stream 62 essentially all of the methanol and/or dimethyl ether content together with that quantity of steam which is desired as a diluent to condition this methanol for feed back to inlet 16 of reactor 10. The bottom stream 62 of this methanol stripper essential comprises that by-product water that formed during the conversion of methanol to olefin composition. As needed, make-up methanol is supplied by line 70 to provide for the total of methanol desired for feed through reactor 10. In the scheme illustrated by FIG. 2 the operations are similar except that due to the placement of the hot fans only the recycles of the product gas compositions are slightly recompressed and there occurs a progressive drop of total pressure through the series of reactors.

With respect to the hot fans used in this process, the fan itself is one of normal design and constructed of materials able to withstand temperatures up to 1050° F. However, the glands of the fan are supplied with steam-fed lanterns, thus keeping the glands at a substantially lower operating temperature.

As fresh feed to the first stage reactor of the series, a large amount of diluent, such as steam, is added to the fresh feed methanol so as to produce a partial pressure of methanol in this fresh feed of 0.1 to about 0.3 ata. This fresh feed of methanol and diluent, when combined with a portion of the product gas of this reactor which is recycled for back-mixing to the reactor inlet then provides for a total composition within the first reactor such that the initial partial pressure of methanol (as the sum of fresh and recycle methanol) is between 0.02 and 0.2 ata. With methanol at this low partial pressure, one may readily regulate the degree of conversion of total methanol (i.e., the sum of fresh feed and recycle methanol) to a low level by (1) operating at higher or lower methanol partial pressures, and further in the reactor system (2) by regulating the space velocity of the gas composition passed through a reactor by blocking off part of the catalyst, for instance through the use of parallel reactor systems (a common practice to stabilize variations in production) and/ or (3) by varying the quantity of the total product gas recycled to the inlet reactor side for back-mixing with the fresh feed of methanol and diluent. As a ratio of recycle to bleed off of the total product gas of a reactor, a ratio of 8/1 to 12/1 volume to volume is suitable, a ratio of 11/1 being preferred.

For each reactor after the first, the total feed to such reactor will comprise a quantity of fresh methanol, a bleed product stream containing a quantity of unreacted methanol and/or dimethyl ether from its preceding reaction and a recycle quantity of the product gas of this reactor itself which too contains a quantity of unreacted methanol and/or dimethyl ether. Accordingly, in each of the second, third and/or fourth reactors of the sequence that quantity of methanol fed into contact with the MTO catalyst therein may be considered on the basis of total methanol (sum of fresh, bleed and recycle methanol), total non-product methanol (sum of fresh and bleed methanol), or total fresh methanol added. On the basis of total methanol the conversion thereof within any reactor is maintained at from about 7–8%; on the basis of total non-product methanol the conversion thereof is maintained at from about 40–60%; and on the basis of total fresh methanol added, the conversion in reactors after the first is maintained at $\geq$90% thereof.

Relative to the total sum of fresh methanol added to the series of back-mixed fixed MTO catalyst bed reactors, that quantity of initial diluent, as steam and/or a non-reactive organic compound, added to that quantity of fresh methanol would provide for a relatively low partial pressure of total fresh methanol in this fresh methanol-diluent feed to about 0.1 to 0.3 ata. This feed methanol partial pressure is immediately reduced by the contact of this feed with the large recycle of olefin product gas from this initial partial pressure to a value approaching that of the exit partial pressure of methanol in the product gas composition. This happens in each of the several reactors in series, be they two, three or four. Thus, the relatively high inlet partial pressure of (0.1 to 0.3) fresh feed methanol is never itself in contact with catalyst particles even in the first reactor, thus reducing considerably the rate of coke formation in the first and any sequence reactor. In this manner, as demonstrated in the Example 1, the partial pressure of methanol either in the inlet or in the outlet of any reactor, is between 0.03 and 0.07 ata. If it were desirable to attain even a much lower partial pressure, that would also be possible.

But as indicated before, a very low partial pressure of methanol would appear to carry with it two apparent negatives. In the first instance a much higher catalyst inventory would seem to be necessary because the rate of methanol conversion is slowed down with the lowering of the methanol partial pressure. Also, with the slowing down of the methanol reaction the conversion of the ethylene to propylene stays at full force. Thus the yield in ethylene seems to go down. However, the process as here proposed makes it possible to attain an intermediate value for the methanol partial pressure in all reactors and at the same time the ethylene partial pressure in the first reactor is less than in the second one, and again that ethylene partial pressure is lower in the second reactor than in the third and again for the third and the fourth. Thus, at about constant methanol partial pressure in all reactors the side reaction that converts ethylene to propylene is suppressed in the early reactors, while the conversion rate of methanol is about constant in all reactors.

Under the conditions as stated, for a three-reactor series a 70% or greater conversion of fresh feed methanol can be realized with a yield to ethylene based upon fresh methanol carbon feed minus recoverable unconverted methanol of greater than 70%; for a four-reactor series a 76% or greater conversion of fresh methanol can be realized with a yield to ethylene based upon fresh methanol carbon feed minus recoverable unreacted methanol of greater than 65%. With more reactors the ethylene is obtained at a lower excess of steam.

Under the conditions to which the MTO catalyst in the fixed bed of each reactor of the series is exposed, the deactivating coke build-up thereon should be greatly retarded as a function of unit catalyst per unit time compared to a one pass single fixed bed operation wherein a large catalyst inventory is utilized as the expedient to provide for an acceptable TOS before catalyst regeneration is necessitated.

Consider, for example, that in a one pass single fixed bed procedure wherein a large catalyst inventory is utilized to provide for adequate TOS: if coking of the MTO catalyst is only a linear function of methanol partial pressure then, for a given degree and quantity of input methanol conversion—say, based upon a conversion of 105 lb-moles per hour (MPH) of total fresh methanol feed—coking on the MTO catalyst would be, on an average, linearly proportional to the average methanol partial pressure through the course of its reactor input level to its output level in the exit gas composition. In a one pass single fixed bed procedure—wherein methanol conversion is or exceeds 99%—at an initial input of 105 MPH methanol and 525 MPH steam ($H_2O$) wherein at a total pressure of 1 ata the initial partial pressure of methanol upon first contact with that zone of active MTO catalyst is about 0.1666 ata methanol and the partial pressure of methanol after 90% conversion is 0.0157 ata, then the average of MeOH partial pressure during its 90% conversion is about 0.08964 ata (See Example—Comparative A below).

Were one instead, as here proposed, to proceed as in a manner wherein the initial partial pressure of methanol upon contact what the MTO catalyst was, say about ⅓ of this 0.16666 ata value, such as about 0.055 to 0.060 ata, and one maintained the average partial pressure of methanol in contact with the MTO catalyst on the order of 0.05 to 0.06 ata, then the rate of coking of the MTO catalyst would be no greater than 60% of the one pass single bed conversion of the same quantity of methanol. However, with the process of this invention, an even lesser rate of coke formation may be expected in view of the large excess of steam taken in conjunction with the low total reaction pressure.

Next, again comparing to a one pass single fixed bed operation, with the process of this invention one may use a much smaller catalyst inventory to achieve the same per unit time yield of olefin products or conversion of methanol. Since the rate of methanol conversion over an MTO catalyst is essentially a linear function of methanol partial pressure the relative volume of MTO catalyst required to convert an incremental amount of the methanol is given by the inverse of the methanol partial pressure. As demonstrated in Example-Comparative A, the relative volume of MTO catalyst required to convert about 105 MPH of methanol by one pass through a single fixed bed is about 355 relative volume units. By comparison, as shown in Example 1 a series of four back-mixed fixed bed reactors each containing 42.5 relative volumes of MTO catalyst—for a total of 170—allows for conversion of this same 105 MPH of methanol.

EXAMPLE—COMPARATIVE A

This example presumes that a total of 105 lb. moles per hour (MPH) of methanol as diluted with 525 MPH steam is fed into contact in a single pass with a fixed bed of MTO catalyst, beginning with an inlet total initial pressure of 1 atmospheres absolute (ata) and an inlet temperature of this feed gas composition of 825° F. (441° C.). In the following calculation the reaction gas composition is given at each increment of 10.5 MPH of methanol converted. Also calculated for each increment is the total MPH of gas composition, the partial pressure of methanol, partial pressure of ethylene and the relative volume of catalyst at the partial pressure of methanol at each 10.5 MPH increment of methanol converted. A pressure drop from the inlet to the outlet of the fixed bed reactor of less than 0.05 ata is presumed, but a 1 ata pressure of reaction is assumed in the calculation. Table 1 below reports the results of this calculation.

TABLE 1

| MeOH (MPH) | $C_2H_4$ (MPH) | $C_3H_6$ (MPH) | $C_4H_8$ (MPH) | Steam (MPH) | Total Moles Gas | Partial Pressure MeOH | Partial Pressure $C_2H_2$ | Relative Volume of Catalyst to Convert 10.5 MPH MeOH |
|---|---|---|---|---|---|---|---|---|
| 105 | 0 | 0 | 0 | 525 | 630 | 0.1666 | 0 | 6 |
| 94.5 | 5.25 | 0 | 0 | 535.5 | 635.25 | 0.1488 | 0.0083 | 6.720 |
| 84 | 9.98 | 0.32 | 0.026 | 546 | 640.33 | 0.1312 | 0.0156 | 7.373 |
| 73.5 | 14.18 | 0.74 | 0.236 | 556.5 | 645.16 | 0.1139 | 0.0220 | 8.780 |
| 63 | 17.85 | 1.37 | 0.546 | 567 | 649.77 | 0.0970 | 0.0275 | 10.314 |
| 52.5 | 21 | 2.31 | 0.893 | 577.5 | 654.20 | 0.0803 | 0.0321 | 12.461 |
| 42 | 23.63 | 3.36 | 1.418 | 588 | 658.41 | 0.0638 | 0.0397 | 15.676 |
| 31.5 | 25.2 | 4.41 | 2.468 | 598.5 | 662.08 | 0.0476 | 0.0381 | 21.018 |

TABLE 1-continued

| MeOH (MPH) | $C_2H_4$ (MPH) | $C_3H_6$ (MPH) | $C_4H_8$ (MPH) | Steam (MPH) | Total Moles Gas | Partial Pressure MeOH | Partial Pressure $C_2H_2$ | Relative Volume of Catalyst to Convert 10.5 MPH MeOH |
|---|---|---|---|---|---|---|---|---|
| 21.5 | 26.25 | 6.3 | 3.15 | 609 | 665.7 | 0.0315 | 0.0394 | 31.700 |
| 10.5 | 26.25 | 8.4 | 4.2 | 619.5 | 668.85 | 0.0157 | 0.0457 | 63.700 |
| Totals after 90% Conversion | | | | | | 0.8964 | | 177.742 |
| For 99% + Conversion Total Relative Cat Vol. | | | | | | | | 355.484 |

Example 1

This example presumes that 170 relative units of that volume of MTO catalyst employed in the single fixed bed of Comparative Example A are now equally distributed throughout four fixed beds, each fixed bed thereof being provisioned with a hot fan for slightly recompressing and recycling a portion of its exit product gas composition back to the inlet side of the bed for mixing with a quantity of methanol added thereto to form a feed composition for pass through this fixed bed, while the remaining portion of the exit product gas of this reactor is passed as a bleed feed stream to the inlet side of the next fixed bed in the series. In the first fixed bed reactor of the series the total feed to this first reactor comprises as a sum that quantity of fresh make-up methanol diluted with steam and that portion of this reactor's exit product gas that is recycled by the hot fan back to the reactor inlet. In the second, third and fourth fixed bed reactors the total feed to any one of those reactors comprises as a sum a quantity of fresh make-up methanol, the bleed steam passed thereto from a preceding reactor and that portion of this reactor's exit product gas that is recycled by the hot fan back to the reactor inlet. In the fourth reactor that portion of its exit product gas composition not recycled by its hot fan back to the inlet is the final bleed stream product of the process. This bleed stream product would be processed in a conventional manner to recover its olefin contents as separate product streams and the balance thereof, which is an aqueous methanol stream would be subjected to simple stripping to yield as an overhead stream one of methanol and an amount of steam desired as a diluent for supply as a feed stream to the first reactor and as a bottom liquid stream the water by-product of the MTO reaction.

For this sequence of operation the partial pressure of methanol feed to contact with the MTO catalyst in any bed is maintained to a value of or less than 0.0605 ata while the partial pressure of methanol at the outlet of a reaction is maintained at or greater than 90% of this inlet value. This is achieved by control of the space velocity of passage of the gas through the selected passage width of the fixed catalyst bed in conjunction with the quantity of fresh make-up methanol added and the quantity of reactor exit product gas taken back by hot fan recycle to the inlet side of the reactor. Accordingly, only a relatively narrow passage width of MTO catalyst is needed in any fixed bed and the coking of the catalyst therein is essentially even on all catalyst particles across the width. Further the pressure drop across any bed is low. Finally, the temperature rise over each bed is in the order of 10° F. Temperature rise over the four bed sequence is prevented by appropriated control of the temperature of the fresh methanol feed to each bed or, if desired, a slight cooling of the recycle to each bed (not illustrated).

The Table 2 below reports upon the feed compositions supplied to each of the four reactors, the product gas compositions produced therein and the partial pressures of methanol and ethylene therein at the inlet and outlet sides thereof The conditions assumed are the total feed gas to the first reactor is at an inlet temperature of 825° F., a pressure of 1.1 ata, and at a space velocity of 1 WHSV.

TABLE 2

| Reactor | Component | Fresh MeOH (MPH) | Bleed From Prior Reactor (MPH) | Recycle Product Gas (MPH) | Total Feed (MPH) | Partial Pressure (ata) | Exit Product Gas (MPH) | Partial Pressure (ata) | Bleed to Next Reactor (MPH) |
|---|---|---|---|---|---|---|---|---|---|
| I | MeOH | 50 | — | 250 | 300 | 0.05922 | 275 | 0.05416 | 25 |
| | $C_2H_4$ | — | — | 100 | 100 | 0.01974 | 110 | 0.02166 | 10 |
| | $C_3H_6$ | — | — | 15 | 15 | | 16.5 | | 1.5 |
| | $C_4H_8$ | — | — | 1.25 | 1.25 | | 1.375 | | 0.125 |
| | Steam | 400 | — | 4250 | 4650 | | 4675 | | 425 |
| | Total | 450 | | 4616.25 | 5066.25 | | 5077.875 | | |
| II | MeOH | 27.5 | 25 | 275 | 327.5 | 0.05963 | 302.5 | 0.05496 | 27.5 |
| | $C_2H_4$ | — | 10 | 190 | 200 | 0.03641 | 209 | 0.03797 | 19 |
| | $C_3H_6$ | — | 1.5 | 33.5 | 35 | | 36.85 | | 3.35 |
| | $C_4H_8$ | — | 0.125 | 4.85 | 4.975 | | 5.335 | | 0.485 |
| | Steam | — | 425 | 4500 | 4925 | | 4950 | | 450 |
| | Total | 27.5 | | | 5492.475 | | 5503.685 | | |
| III | MeOH | 27.5 | 27.5 | 300 | 355 | 0.06004 | 330 | 0.05571 | 30 |
| | $C_2H_4$ | — | 19 | 270 | 289 | 0.04888 | 297 | 0.05014 | 27 |
| | $C_3H_6$ | — | 3.35 | 50 | 53.35 | | 55 | | 5 |
| | $C_4H_8$ | — | 0.485 | 15 | 15.485 | | 16.5 | | 1.5 |
| | Steam | — | 450 | 4750 | 5200 | | 522.5 | | 475 |
| | Total | 27.5 | | | 5912.835 | | 5923.5 | | |
| IV | MeOH | 32.5 | 30 | 325 | 387.5 | 0.060501 | 357.5 | 0.05571 | 32.5 |

TABLE 2-continued

| Reactor | Component | Fresh MeOH (MPH) | Bleed From Prior Reactor (MPH) | Recycle Product Gas (MPH) | Total Feed (MPH) | Partial Pressure (ata) | Exit Product Gas (MPH) | Partial Pressure (ata) | Bleed to Next Reactor (MPH) |
|---|---|---|---|---|---|---|---|---|---|
| | $C_2H_4$ | — | 27 | 355 | 382 | 0.05964 | 390.5 | 0.06085 | 35.5 |
| | $C_3H_6$ | — | 5 | 75 | 80 | | 82.5 | | 7.5 |
| | $C_4H_8$ | — | 1.5 | 28.75 | 30.25 | | 31.625 | | 2.875 |
| | Steam | — | 475 | 5050 | 5525 | | 555 | | 505 |
| | Total | 32.5 | | | 6404.75 | | 6417.125 | | 538.375 |

This example is similar to Example 1 except that in Reactor II, III, and IV recycle of a portion of the exit product gas composition over these reactors is eliminated. Again, the unreacted methoxy compound in this exit product gas composition is listed as methanol, but it is to be understood that the unreacted methoxy compound may actually comprise a quantity of dimethyl ether which for partial pressure calculation would count as two units of methanol for each one unit thereof.

The Table 3 below reports upon the feed compositions supplied to each of the four reactors, the product gas compositions produced therein and the partial pressures of methanol and ethylene therein at the inlet and outlet sides thereof. The conditions assumed are the total feed gas to the first reactor is at an inlet temperature of 825° F., a pressure of 1.1 ata, and at a space velocity of 1 WHSV.

low methanol conversion. TOS would be too short with a single fixed bed since a relatively high partial pressure of methanol in the initial feed would be required. By contrast, in the back-mixed series of fixed bed MTO reactors illustrated by Example 1, or in Example 2 wherein only the first reactor is on recycle, after the third reactor to this point 105 MPH of fresh methanol has been added to the initial 400 MPH of dilution steam and to this point has passed through 127.5 relative volume units of MTO catalyst to yield about 70% of ethylene based upon methanol converted. Whereas in the one pass single fixed bed of Comparative A the 70 units of catalyst have been exposed to an average partial pressure of methanol of 0.1145 ata, at this comparable point in the back-mixed series of Example 1 the 127 units of MTO catalyst have been exposed to a partial pressure of methanol no greater than 0.06 ata. Whereas, in the one pass single bed process of Comparative A to convert the remaining 42 MPH

TABLE 3

| Reactor | Component | Fresh MeOH (MPH) | Bleed From Prior Reactor (MPH) | Recycle Product Gas (MPH) | Total Feed (MPH) | Partial Pressure (ata) | Exit Product Gas (MPH) | Partial Pressure (ata) | Bleed to Next Reactor (MPH) |
|---|---|---|---|---|---|---|---|---|---|
| I | MeOH | 50 | — | 250 | 300 | 0.05922 | 275 | 0.05416 | 25 |
| | $C_2H_4$ | — | — | 100 | 100 | 0.01974 | 110 | 0.02166 | 10 |
| | $C_3H_6$ | — | — | 15 | 15 | | 16.5 | | 1.5 |
| | $C_4H_8$ | — | — | 1.25 | 1.25 | | 1.375 | | 0.125 |
| | Steam | 400 | — | 4250 | 4650 | | 4675 | | 425 |
| | Total | 450 | | 4616.25 | 5066.25 | | 5077.875 | | |
| II | MeOH | 27.5 | 25 | | 52.1 | 0.1073 | 27.5 | 0.05484 | 27.5 |
| | $C_2H_4$ | — | 10 | | 10 | 0.018945 | 19 | 0.040154 | 19 |
| | $C_3H_6$ | — | 1.5 | | 1.5 | | 3.35 | | 3.35 |
| | $C_4H_8$ | — | 0.125 | | 1.25 | | 0.485 | | 0.485 |
| | Steam | — | 425 | | 425 | | 450 | | 450 |
| | Total | 27.5 | | | 489.125 | | 500.335 | | |
| III | MeOH | 27.5 | 27.5 | | 55 | 0.10420 | 30 | 0.05571 | 30 |
| | $C_2H_4$ | — | 19 | | 19 | 0.035996 | 27 | 0.05014 | 27 |
| | $C_3H_6$ | — | 3.35 | | 3.35 | | 5 | | 5 |
| | $C_4H_8$ | — | 0.485 | | 0.485 | | 1.5 | | 1.5 |
| | Steam | — | 450 | | 450 | | 475 | | 475 |
| | Total | 27.5 | | | 527.835 | | 528.5 | | |
| IV | MeOH | 32.5 | 30 | | 62.5 | 0.109457 | 32.5 | 0.05571 | 32.5 |
| | $C_2H_4$ | — | 27 | | 27 | 0.06852 | 35.5 | 0.0685 | 35.5 |
| | $C_3H_6$ | — | 5 | | 5 | | 7.5 | | 7.5 |
| | $C_4H_8$ | — | 1.5 | | 1.5 | | 2.875 | | 2.875 |
| | Steam | — | 475 | | 475 | | 505 | | 505 |
| | Total | 32.5 | | | 571 | | 583.375 | | 538.375 |

By comparing the values given in the Table 1 for the Comparative A Example with those for Example 1 one will see that in a one pass single bed conversion of a methanol feed diluted with steam to a ratio of ⅛ and admitted at 1 ata of total pressure that an instantaneous partial pressure of methanol approaches the 0.06 ata level at the 60% methanol conversion level at which point the methanol-steam feed has progressed through about 70 relative volume units of MTO catalyst, at which point the yield of ethylene based upon methanol conversion is about 75%. It is, however, not feasible to operate a standard single fixed bed with such a of methanol requires a further 285 relative volume units of MTO catalyst, such that the MeOH converted as a ratio to catalyst volume is 105/355=0.295; in the back-mixed series of reactors illustrated in Example 1 only 170 relative volume units of MTO catalyst are needed to achieve a conversion of 105 MPH methanol such that the ratio of converted MeOH to catalyst volume of 105/170=0.618.

With the process of this invention the same quantity of MeOH may be converted per unit time with a much reduced inventory of MTO catalyst which will coke to inactivity at a much slower rate than that which would be possible by a one-pass single bed process operation.

What is claimed is:

1. A process for converting a methoxy compound to olefin products, comprising:

adding a first quantity of methoxy compound and a non-reactive diluent to a portion of an olefin product gas composition formed by methoxy compound contact with a fixed bed of MTO catalyst in a first reaction vessel to form a feed to contact with said MTO catalyst in said first fixed bed such that the partial pressure of methoxy compound as initially contacted with said MTO catalyst of said first fixed bed is between 0.02 and 0.2 ata and the partial pressure of methoxy compound in the olefin product gas composition exiting from said first fixed MTO catalyst bed is at least 90% of the initial value of partial pressure of methoxy compound in the total feed, and routing a bleed portion of said olefin product gas composition formed in said first fixed bed reactor to an inlet of a second fixed bed reactor;

adding a second quantity of methoxy compound into a mixture with said bleed portion of an olefin product gas composition from said first reaction vessel and with a portion of olefin product gas composition formed by methoxy compound contact with a fixed bed of MTO catalyst in a second reaction vessel to form a feed to contact with said MTO catalyst in said second fixed bed such that the partial pressure of methoxy compound as initially contacted with said MTO catalyst of said second fixed bed is between 0.02 and 0.2 ata and the partial pressure of methoxy compound in the olefin product gas composition exiting from said second fixed MTO catalyst bed is at least 80% of the initial inlet value of partial pressure of methoxy compound, and routing a bleed portion of said olefin product gas composition formed in said second fixed bed reactor to another location.

2. The process of claim 1, further comprising the step of adding a third quantity of methoxy compound into a mixture with said bleed portion of olefin product gas composition formed in said second fixed bed reactor and with a portion of an olefin product gas composition formed by methoxy compound contact with a fixed bed of MTO catalyst in a third reaction vessel to form a feed to contact with said MTO catalyst in said third fixed bed such that the partial pressure of methoxy compound as initially contacted with said MTO catalyst of said third fixed bed is between 0.02 and 0.2 ata and the partial pressure of methoxy compound in the olefin product gas composition exiting from said third fixed MTO catalyst bed is at least 80% of the initial value of partial pressure of methoxy compound; and recovering a bleed portion of said olefin product gas composition formed in said third fixed bed reactor.

3. A process for converting a methoxy compound to olefin products, comprising:

adding a first quantity of methoxy compound and a non-reactive diluent to a portion of an olefin product gas composition formed by methoxy compound contact with a fixed bed of MTO catalyst in a first reaction vessel to form a feed to contact with said MTO catalyst in said first fixed bed such that the partial pressure of methoxy compound as initially contacted with said MTO catalyst of said first fixed bed is between 0.02 and 0.2 ata and the partial pressure of methoxy compound in the olefin product gas composition exiting from said first fixed MTO catalyst bed is at least 80% of the initial value of partial pressure of methoxy compound, and routing a bleed portion of said olefin product gas composition formed in said first fixed bed reactor to an inlet of a second fixed bed reactor;

adding a second quantity of methoxy compound into a mixture with said bleed portion of an olefin product gas composition from said first reaction vessel and with a portion of olefin product gas composition formed by methoxy compound contact with a fixed bed of MTO catalyst in a second reaction vessel to form a feed to contact with said MTO catalyst in said second fixed bed such that the partial pressure of methoxy compound as initially contacted with said MTO catalyst of said second fixed bed is between 0.02 and 0.2 ata and the partial pressure of methoxy compound in the olefin product gas composition exiting from said second fixed MTO catalyst bed is at least 80% of the initial inlet value of partial pressure of methoxy compound, and routing a bleed portion of said olefin product gas composition formed in said second fixed bed reactor to an inlet of a third fixed bed reactor;

adding a third quantity of methoxy compound into a mixture with said bleed portion of olefin product gas composition formed in said second fixed bed reactor and with a portion of an olefin product gas composition formed by methoxy compound contact with a fixed bed and MTO catalyst in a third reaction vessel to form a feed to contact with said MTO catalyst in said third fixed bed such that the partial pressure of methoxy compound as initially contacted with said MTO catalyst of said third fixed bed is between 0.02 and 0.2 ata and the partial pressure of methoxy compound in the olefin product gas composition exiting from said third fixed MTO catalyst bed is at least 80% of the initial value of partial pressure of methoxy compound; and routing a bleed portion of said olefin product gas composition formed in said third fixed bed reactor to an inlet of a fourth fixed bed reactor; and adding a fourth quantity of methoxy compound into a mixture with said bleed portion of an olefin product gas composition formed in said third fixed bed reactor and with a portion of olefin product gas composition formed by methoxy compound contact with a fixed bed of MTO catalyst in a fourth reaction vessel to form a feed to contact with said MTO catalyst in said fourth fixed bed such that the partial pressure of methoxy compound as initially contacted with said MTO catalyst of said fourth fixed bed is between 0.02 and 0.2 ata and the partial pressure of methoxy compound in the olefin product gas composition exiting from said fourth fixed MTO catalyst bed is at least about 80% of the initial value of partial pressure of methoxy compound, and recovering a bleed portion of said olefin product gas composition formed in said fourth fixed bed reactor.

4. A process for converting a methoxy compound to olefin products, comprising:

adding a first quantity of methoxy compound and a non-reactive diluent to a portion of an olefin product gas composition formed by methoxy compound contact with a fixed bed of MTO catalyst in a first reaction vessel to form a feed to contact with said MTO catalyst in said first fixed bed such that the partial pressure of methoxy compound as initially contacted with said MTO catalyst of said first fixed bed is between 0.02 and 0.2 ata and the partial pressure of methoxy compound in the olefin product gas composition exiting from said first fixed MTO catalyst bed is at least 90% of the initial value of partial pressure of methoxy compound in the total feed, and routing a bleed portion of said olefin product gas composition formed in said first fixed bed reactor to an inlet of a second fixed bed reactor;

adding a second quantity of methoxy compound into a mixture with said bleed portion of an olefin product gas composition from said first reaction vessel to form a feed to contact with said MTO catalyst in said second fixed bed such that the partial pressure of methoxy compound as initially contacted with said MTO catalyst of said second fixed bed is between 0.02 and 0.2 ata and the partial pressure of methoxy compound in the olefin product gas composition exiting from said second fixed MTO catalyst bed is at least 40% of the initial inlet value of partial pressure of methoxy compound.

* * * * *